United States Patent [19]

Carter

[11] 4,009,221
[45] Feb. 22, 1977

[54] HF RECOVERY WITH ALKYL FLUORIDE FORMATION AND UTILITY IN ALKYLATION

[75] Inventor: Cecil O. Carter, Wann, Okla.

[73] Assignee: Phillips Petroleum Company, Bartlesville, Okla.

[22] Filed: June 19, 1975

[21] Appl. No.: 588,558

Related U.S. Application Data

[62] Division of Ser. No. 327,734, Jan. 29, 1973, Pat. No. 3,906,051.

[52] U.S. Cl. .................... 260/683.48; 260/683.41; 260/653.6
[51] Int. Cl.² .......................................... C07C 3/54
[58] Field of Search ................ 260/683.48, 683.49, 260/683.42, 653.6

[56] References Cited

UNITED STATES PATENTS

| | | | |
|---|---|---|---|
| 2,342,677 | 2/1944 | Linn | 260/683.48 |
| 2,384,735 | 9/1945 | Frey | 260/683.48 |
| 2,417,875 | 3/1947 | Leonard | 260/683.41 |
| 2,425,745 | 8/1947 | Leonard et al. | 260/683.41 |
| 3,716,593 | 2/1973 | Hutson, Jr. et al. | 260/653.6 |
| 3,845,158 | 10/1974 | Sobel | 260/683.49 |
| 3,959,402 | 5/1976 | Mikulicz et al. | 260/683.48 |

OTHER PUBLICATIONS

B526,027, Feb. 1976, Mikulicz et al., 260/683.48

*Primary Examiner*—George Crasanakis

[57] ABSTRACT

A process and apparatus for HF alkylation wherein the vapor from the fractionation zone in which the effluent of the reaction zone is fractionated is contacted with water, the mixture formed is reacted with an olefin to form an alkyl fluoride, the alkyl fluoride is recovered and reintroduced into the alkylation reaction zone.

3 Claims, 1 Drawing Figure

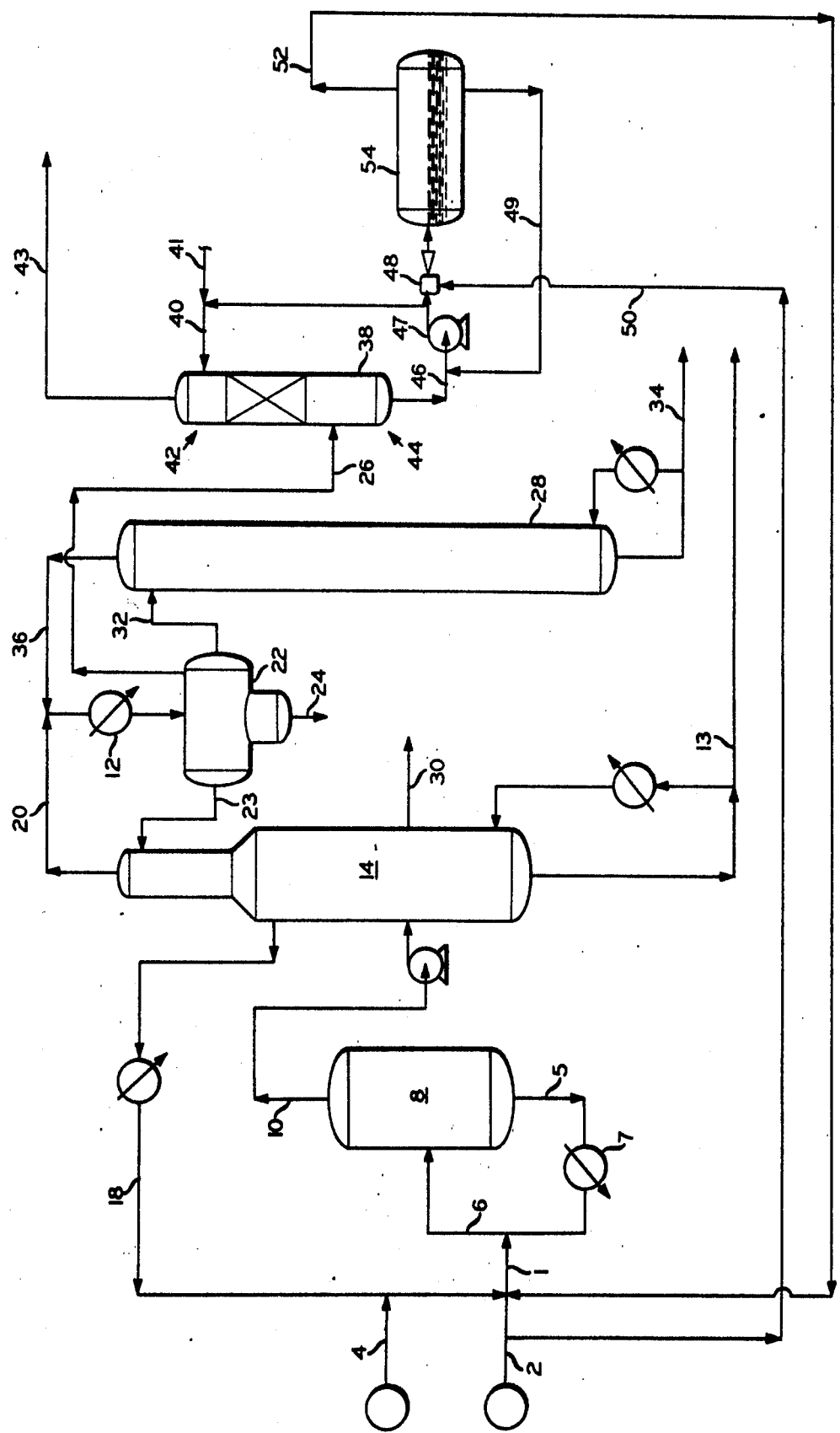

HF RECOVERY WITH ALKYL FLUORIDE FORMATION AND UTILITY IN ALKYLATION

This application is a division application of Ser. No. 327,734, filed Jan. 29, 1973, now U.S. Pat. No. 3,906,051.

In order to prevent waste of valuable catalyst and to minimize emissions of catalyst into the atmosphere or other processing systems, it is desirable to provide an apparatus and method for recovering hydrogen fluoride, used, for example, as a catalyst in HF alkylation, from a vapor stream containing hydrogen fluoride. This invention therefore resides in apparatus and process for removing hydrogen fluoride from a hydrogen fluoride-containing vaporous stream and recovering said hydrogen fluoride.

Other aspects, objects, and advantages of the present invention will become apparent from a study of the disclosure, the appended claims, and the drawing.

The drawing is a diagrammatic view of an HF alkylation system having apparatus for recovery of HF from a vaporous stream.

Referring to the drawing, an olefin feed stream 2, an isobutane feedstream 4, and an HF catalyst stream 5 are charged to reactor 6 wherein alkylation of the isobutane with olefin occurs. The reaction mass or emulsion comprising alkylation product passes from reactor 6 into settler 8, wherein a lower liquid HF catalyst phase forms and is removed via 5 and cooler 7 and is recycled to reactor 6; and an upper liquid hydrocarbon phase, including alkylation product, saturated with HF, forms. This hydrocarbon phase passes via conduit 10 to reboiled fractionator 14. Debutanized alkylation product is recovered from fractionator 14 via conduit 13; a side draw of vaporous normal butane is removed via conduit 30; and a side draw of liquid isobutane stream is removed via conduit 18 and is recycled to the reaction zone 6. Overhead vapors, from fractionator 14, comprising propane and lighter hydrocarbons and hydrogen fluoride containing stream pass via conduit 20 and condenser 12 into overhead accumulator 22 wherein a lower liquid HF phase is formed, an upper liquid hydrocarbon phase is formed, and noncondensibles are present above the hydrocarbon phase. The liquid HF phase is removed via conduit 24 and recycled (not shown) to reactor 6. A portion of the liquid hydrocarbon phase 23 is used to reflux the upper portion of fractionator 14. Another portion of the liquid hydrocarbon phase, sufficient to rid the system of charged and produced propane, is charged via conduit 32 to the HF stripper 28. Product propane, substantially free of HF is recovered via 34. Vaporous HF and propane are removed from the HF stripper 28 via conduit 36 and are combined with the overhead vapors 20 from fractionator 14 upstream of the condenser 12. Noncondensibles are removed from accumulator 22 via conduit 26. This vaporous stream 26 comprises light hydrocarbons and hydrogen fluoride. This vapor stream 26 cannot be used, e.g., as fuel gas, because of its HF content.

Hydrogen fluoride containing vapor stream 26 is charged to the lower end portion 44 of absorption column 38 having an upper end portion 42 and a lower end portion 44. This column can have contact trays, inert packing and the like to effect proper contact. A water stream 40 passes into an upper end portion 42 of absorber 38 wherein the downflowing water stream countercurrently contacts the rising vapor stream 26 and removes the hydrogen fluoride from the vapor stream, producing hydrocarbon vapors substantially free of HF, removed from the absorber 38 via conduit 43. This stream 43 can now be used as fuel gas since it is not contaminated with HF. The HF-water extract stream produced in absorber 38 is removed from the lower end portion of absorber 38 via conduit 46 as the first mixture stream and passed to pump 47 along with an HF-water phase 49 described hereinbelow. A portion of the effluent from pump 47 is returned to conduit 40. Makeup water, as needed may be added to conduit 40 via conduit 41. The remainder of the effluent from pump 47 is passed to a reaction zone, in this example represented by an eductor 48, to which is charged a portion of the olefin feed, or other olefin, via conduit 50. In reactor 48, the olefin reacts with the HF which is present in the HF-water extract stream 46, and the mass is passed to separator 54 wherein an upper liquid alkyl fluoride phase forms and wherein a lower water phase forms which is now leaner in HF. This now leaner in HF-water phase is recycled via conduit 49 to pump 47. The produced alkyl fluoride stream is passed via conduit 52 to the reaction zone wherein it is converted into additional alkylate by reaction with isobutane therein.

Reaction conditions in reactor 48 are preferably at a pressure not greater than about 300 psig, preferably in the range of about 150 to 200 psig, and a temperature range of about 50° F to about 150° F, preferably at about 90° F to 110° F. The olefin to HF weight ratio is preferably about 5 to 1 to about 40 to 1 in order to react out the HF from the HF-water extract stream. Preferably the olefin used is isobutylene, but can include any one of propylene, isobutylene, a butylene, and amylenes. Examples of the butylenes can be butene-1, cis-butene-2, and trans-butene-2. The olefin is preferably added in the liquid form. Recycle of the liquid phase 49 to reaction zone 48 assists in the reaction.

Reactor 6 is operated at a pressure to maintain substantially liquid phase, e.g., above about 150 psig, and at a temperature in the range of about 70° to 150° F, usually at about 90° to 110° F, which allows use of water as the cooling medium in exchanger 7. The isobutane to olefin (plus alkyl fluoride) mol ratio is usually in the range of 4 to 1 up to 25 to 1, preferably about 8 to 1 to 15 to 1. The volume ratio of HF catalyst to total hydrocarbon is usually about 1 to 1 up to about 8 to 1, usually about 4 to 1 to 6 to 1. These conditions produce the highest octane alkylate.

The absorber 38 is operated in the temperature range of about 50° F to about 150° F, more preferably at about 90° F to 110° F, and at a pressure less than about 300 psig, preferably in the range of about 150 to 200 psig. The mol ratio of aqueous phase 40 to mols of HF in stream 26 is usualy about 1 to 1 to about 5 to 1. It is desirable to maintain the concentration of HF in the HF-water extract 46 above about 15 weight percent, more preferably above about 25 weight percent, up to about 50 weight percent.

The olefin feed stream 2 can be one of propylene, a butylene, isobutylene, and amylenes, or mixtures thereof. The isoparaffin can be isobutane and/or isopentane.

TYPICAL PLANT OPERATION

The vapor stream 26 charged to absorber 38 has the following typical composition:

| Component | Pounds/Day |
|---|---|
| Ethane | 396 |
| Propane | 2073 |
| Hydrogen Fluoride | 50 |

The vent gas 43 removed from the absorber 38 has the following composition:

| Component | Pounds/Day |
|---|---|
| Ethane | 396 |
| Propane | 2073 |
| Hydrogen Fluoride | Nil |

The HF-water scrubbing liquid has the following composition:

| Component | Pounds/Day |
|---|---|
| Water | 150 |
| Hydrogen Fluoride | 50 |

The HF-water extract yield 46 has the following composition:

| Component | Pounds/Day |
|---|---|
| Water | 150 |
| Hydrogen Fluoride | 100 |

Absorber 38 is operated at about 100° F and about 200 psig.

Reactor 48 charges about 27.5 barrels per day of liquid olefin (about 50 weight percent olefin) which amounts to about 2800 pounds per day of olefins, and with recycle 49 the HF-water charged to reactor 48 is about 450 pounds per day, containing about 100 pounds of HF therein. The reacton is effected in the eductor-mixer 48 at about 100° F at about 200 psig. Alkyl fluoride produced (equivalent to 50 pounds/day of HF) and unreacted olefin stream is recovered from settler 54 via conduit 52 and charged to reaction zone 6. The HF-water phase 49 comprising about 450 pounds per day water and 100 pounds per day HF is recycled to conduit 46.

EXAMPLE I

Reaction of Pure Isobutylene with Solutions of HF Acid and the Formation of Isobutyl Fluoride

| HF Concentration, Wt. % in Water | | 9.5 | 20 | 30 | 40 | 53 |
|---|---|---|---|---|---|---|
| Olefin Feed Composition, Wt. % | | | | Average Product | | |
| isobutane | 0.04 | 0.04 | 0.03 | 0.04 | 0.31 | 0.06 |
| normal-Butane | 0.0 | — | — | 0.01 | 0.05 | 0.01 |
| Isobutylene + Butene-1 | 99.9 | 99.89 | 97.43 | 88.17 | 14.0 | 2.15 |
| trans-Butene-2 | 0.05 | 0.04 | 0.04 | 0.05 | 0.51 | 0.10 |
| cis-Butene-2 | — | — | 0.01 | 0.03 | 0.16 | 0.01 |
| Isobutyl Fluoride | — | 0.03 | 2.49 | 11.6 | 84.59 | 96.45 |
| Residue | — | — | — | 0.1 | 0.38 | 1.22 |
| Total | 99.9 | 100.00 | 100.00 | 100.00 | 100.00 | 100.00 |
| Isobutylene Conversion, Wt. % | | 0.01 | 1.91 | 8.97 | 81.98 | 97.12 |
| Isobutyl Fluoride Selectivity | | 100 | 100 | 98.4 | 97.9 | 98.2 |

The olefin feed utilized was a mixture of isobutylene and butene-1.

This example illustrates that the concentration of HF in water should be above about 20 weight percent to effect preferred economical recovery of HF from water containing HF using an olefin containing stream.

EXAMPLE II

Reaction of Mixed Propylene-Butylene Olefins with Solutions of HF Acid in Water to Produce Alkyl Fluorides

| HF Concentration, Wt. % in Water | 30 | 52 | 60 |
|---|---|---|---|
| Olefin Feed Composition, Wt. % | | Average Product | |

EXAMPLE II-continued

Reaction of Mixed Propylene-Butylene Olefins with Solutions of HF Acid in Water to Produce Alkyl Fluorides

| | | | | |
|---|---|---|---|---|
| Propane | 12.3 | 12.1 | 11.9 | 11.6 |
| Propylene | 21.7 | 21.4 | 21.0 | 16.6 |
| Isobutane | 27.6 | 28.3 | 25.8 | 28.6 |
| n-Butane | 7.6 | 7.4 | 8.0 | 7.3 |
| Isobutane + Butene-1 | 15.5 | 11.5 | 7.3 | 7.0 |
| trans-Butene-2 | 8.4 | 8.2 | 8.8 | 8.3 |
| cis-Butene-2 | 6.1 | 5.8 | 6.1 | 4.1 |
| Isobutyl Fluoride | — | 4.7 | 9.7 | 10.7 |
| 2-Fluorobutane | — | — | 0.6 | 4.1 |
| Residue | 0.8 | 0.5 | 0.7 | 1.9 |
| Olefin Conversion, Wt. % | — | 8.1 | 14.0 | 27.7 |
| Fluoride Selectivity, % | — | 83.2 | 100.0 | 76.1 |
| Olefin Feed Purity | 51.7 wt. % olefin | | | |
| Olefin Density | 4.7242 Lbs/Gal. (olefins only) | | | |

This example illustrates that as the concentration of HF in the water increases, the conversion of the olefins to alkyl fluoride increases, but that above about 52 weight percent HF in water, the selectivity to fluorides decreases.

TABLE I

The following is a calculated material balance of the process:

| Unit Capacity | 4000 BPD alkylate |
|---|---|
| Ethane vent | 0.75 BBL/1000 BBL alkylate |
| Alkylate yield | 1.8 BBL/BBL Olefin |
| iC$_4$/olefin ratio | 13 BBLS/BBL |
| Olefin purity | 51.7 wt. % |

HF Containing Vapor Stream (26)

| Component | Mole % | Wt. % | Lbs/Day |
|---|---|---|---|
| Ethane | 21 | 15.72 | 396 |
| Propane | 75 | 82.29 | 2073 |
| HF Vapor | 4 | 1.99 | 50 |
| Total | 100 | 100.00 | 2519 |

Liquid Olefin Stream (50)

| Component | Wt. % | Lbs/Day |
|---|---|---|
| Propane | 12.3 | 667.5 |
| Propylene | 21.7 | 1177.6 |
| Isobutane | 27.6 | 1497.8 |
| normal-Butane | 7.6 | 412.4 |
| Isobutylene + Butene-1 | 15.5 | 841.1 |
| trans-Butene-2 | 8.4 | 455.8 |
| cis-Butene-2 | 6.1 | 331.0 |
| Residue | 0.8 | 43.4 |
| Total | 100.0 | 5426.6 |
| Volume (total feed) | | (275 BPD) |
| (olefin only) | | (14.1 BPD) |

Reasonable variations and modifications, which will be apparent to those skilled in the art, can be made in this invention without departing from the spirit and scope thereof.

What is claimed is:

1. A process for the production of an alkylate comprising:
   a. introducing an isoparaffin selected from the group consisting of isobutane, isopentane and mixtures thereof and an olefin selected from the group consisting of propylene, butylene, isobutylene, amylenes and mixtures thereof and an HF catalyst into an alkylation reaction zone,
   b. reacting the materials introduced into said alkylation reaction zone to form an effluent comprising an alkylate,
   c. separating said effluent into an HF catalyst phase and a hydrocarbon phase,
   d. passing said hydrocarbon phase into a fractionation zone,
   e. withdrawing said alkylate from said fractionation zone as a liquid,
   f. withdrawing a vapor comprising light hydrocarbons and HF from said fractionation zone,
   g. contacting said vapor from said fractionation zone with water to form a vapor stream of light hydrocarbons substantially free of HF and a stream of a liquid first mixture comprising HF and water,
   h. reacting said stream of a liquid first mixture with an olefin selected from the group consisting of propylene, isobutylene, cis-butene-2, trans-butene-2, butene-1, amylenes and mixtures thereof to form an alkyl fluoride comprising reaction product,
   i. separating said alkyl fluoride from said reaction product, and
   j. introducing said alkyl fluoride into the alkylation reaction zone.

2. A process in accordance with claim 1 wherein said vapor from said fractionation zone is contacted with said water at a pressure not greater than 300 psig and at a temperature of about 50° F to about 150° F and wherein said stream of a liquid first mixture is reacted with said olefin in an olefin to HF weight ratio in the range of 5:1 to 40:1, at a pressure not greater than 300 psig, and at a temperature in the range of about 50° F to about 150° F.

3. A process in accordance with claim 1 wherein said vapor is contacted with said water in an absorber.